(12) United States Patent
Poulad

(10) Patent No.: US 12,390,104 B2
(45) Date of Patent: Aug. 19, 2025

(54) ENHANCED EYE TRACKING USING LENS INVERSE TRANSFORM

(71) Applicant: Microsoft Technology Licensing, LLC, Redmond, WA (US)

(72) Inventor: Navid Poulad, San Jose, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 628 days.

(21) Appl. No.: 17/824,663

(22) Filed: May 25, 2022

(65) Prior Publication Data
US 2023/0380683 A1    Nov. 30, 2023

(51) Int. Cl.
| | |
|---|---|
| A61B 3/113 | (2006.01) |
| A61B 3/02 | (2006.01) |
| A61B 3/024 | (2006.01) |
| A61B 3/10 | (2006.01) |
| A61B 3/14 | (2006.01) |
| G02B 27/00 | (2006.01) |
| G02B 27/01 | (2006.01) |

(52) U.S. Cl.
CPC ............. *A61B 3/113* (2013.01); *A61B 3/14* (2013.01); *G02B 27/0093* (2013.01); *G02B 27/017* (2013.01); *G02B 2027/0178* (2013.01)

(58) Field of Classification Search
CPC .......... A61B 3/02; A61B 3/113; A61B 3/102; A61B 3/1015; A61B 3/1225; A61B 3/024; A61B 3/005
USPC ....... 351/209, 200, 205, 206, 210, 221–223, 351/245–246
See application file for complete search history.

(56) References Cited

U.S. PATENT DOCUMENTS

| | | |
|---|---|---|
| 10,509,466 B1 | 12/2019 | Miller et al. |
| 11,150,437 B1 | 10/2021 | Ebert |
| 2016/0210783 A1 | 7/2016 | Tomlin et al. |
| 2018/0144483 A1* | 5/2018 | Kang ..................... G06V 10/50 |

FOREIGN PATENT DOCUMENTS

WO    2007043954 A1    4/2007

OTHER PUBLICATIONS

"International Search Report and Written Opinion Issued in PCT Application No. PCT/US23/017243", Mailed Date: Jul. 12, 2023, 11 Pages.

* cited by examiner

*Primary Examiner* — Dawayne Pinkney
(74) *Attorney, Agent, or Firm* — Schwegman Lundberg & Woessner, P.A.

(57) ABSTRACT

A computer implemented method includes receiving images of an eye through a vision correcting lens via a camera in a head mounted display device, obtaining an inverse transform corresponding to the vision correcting lens, applying the inverse transform to the received images to obtain uncorrected images of the eye, and performing eye tracking based on the uncorrected images of the eye.

20 Claims, 4 Drawing Sheets

ENHANCED EYE TRACKING USING LENS INVERSE TRANSFORM

BACKGROUND

Eye tracking in head mounted virtual reality (VR) displays uses a camera to obtain images from which human eye movement can be determined. Eye trackers can measure the orientation of the eye to determine where a wearer is looking or focusing in a real or virtual scene. Such measurements may be used to interact with VR applications by allowing selection of functions and providing data related to objects being gazed upon.

SUMMARY

A computer implemented method includes receiving images of an eye through a vision correcting lens via a camera in a head mounted display device, obtaining an inverse transform corresponding to the vision correcting lens, applying the inverse transform to the received images to obtain uncorrected images of the eye, and performing eye tracking based on the uncorrected images of the eye.

DETAILED DESCRIPTION

Figure 1:
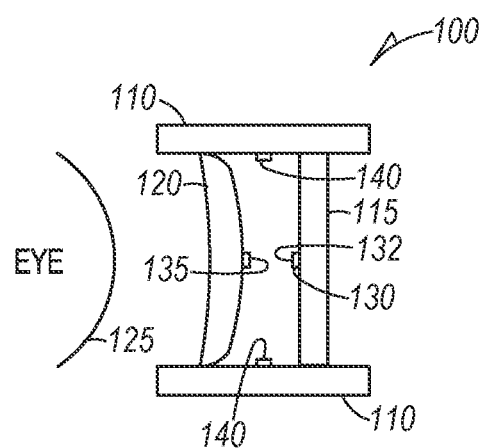
FIG. 1 is a block diagram cross section of a portion of a head mounted device according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware-based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using, software, hardware, firmware, or the like. The terms, "component," "system," and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture," as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

Eye tracking in head mounted devices uses a camera to obtain images from which human eye movement can be determined. Eye trackers can measure the orientation of the eye to determine where a wearer is looking or focusing in a real or virtual scene. Such measurements may be used to interact with mixed realty (MR), augmented reality (AR), and virtual reality (VR) applications by allowing selection of functions and providing data related to objects being gazed upon through a see-through display.

During manufacture, see-through displays may be calibrated to ensure optimal measurements for sensors, including eye tracking sensors. Prescription lenses may be used with see-through displays, but can interfere with the calibrated state of the tracking cameras, and therefore affect the measurements of eye orientation, as light from the eyes may be refracted by the prescription lenses prior to reaching a camera lens.

An improved head mounted display device accommodates prescription lenses and applies an inverse transform associate with optical parameters of the lenses to correct for refraction of light by the lenses. The inverse transform may be programmed into eye tracking software via user-input prescription settings, or may be obtained based on marker on the prescription lenses by the eye tracking camera. The marker may be read and decoded to obtain prescription parameters or an index used to access the corresponding inverse transforms for each of left and right lenses. In one example, the marker may be an infrared (IR) marker that is not visible to a human, but readable by a camera with IR capabilities.

FIG. 1 is a block diagram cross section of a portion of a head mounted device 100. A frame 110 supports both a see-through display 115 and a prescription or vision correcting lens 120 spaced from the see-through 115. The see-through 115 may be a see-through display for an MR or Ar type of head mounted device 100 allowing a user's eye 125 to see through the prescription lens 120 and see-through 115.

An eye tracking camera 130 may be supported at an edge of see-through 115, such as in or near a nose pad of the device 100 for supporting device 100 on a nose of a user wearing the device 100. The camera 130 is positioned between the see-through 115 and the vision correcting lens 120. This position of the camera 130 places it at an edge of a field of view of eye 125 such that it does not interfere with views through the lens 120 and see-through 115.

The camera has an objective lens 132 mounted less than 2 cm from the vision correcting lens in one example. The camera 130 may have a field of view of at least 70 degrees in one example. In one example, a marker 135 is positioned on the lens 120. The marker 135 may be and IR marker printed in IR ink that fluoresces in the infrared range of light that is visible to the camera 130 but is not visible to the human eye. The fluorescence may be caused by IR light that may be provided by one or more IR light emitting diodes 140 located on the frame 110 between the lens 120 and see-through 115.

In further examples, the marker may be silk-screened, printed, or otherwise applied to the Rx lens, using any type of paint such as IR-reflective but visible-light-see-through, or just an ordinary visible ink. The position and size of a visible marker 135 may be configured to minimize obstruction of a view of the user.

The marker 135 may be a QR code or other software recognizable text of other marking that can be used to identify and obtain an inverse transform to correct the camera 130 images of the eye 125 that resulted from lens 120 refracted light received from the eye 125. The corrected images may be used for eye tracking. The marker 135 comprises a prescription in one example.

The QR code may encode information comprising vision correcting information used to identify the inverse transform. The QR code in one example is a 4 mm×4 mm QR code.

In one example, the marker encodes an actual prescription, specifying optical correction parameters such as sphere, cylinder, and axis. Each of these parameters may cause refraction of light, effectively changing where light from the eye impinges on a camera 130 sensor. The corresponding inverse transform may be used to essentially transform the resulting sensed image to correspond to an image of the eye as if light from the eye had not been refracted by the lens.

The parameters may be used identify an inverse transform that most closely will correctly transform the image sensed by the camera 130 into a corrected image. In one example, each 0.25 increment of sphere diopter may be associated with a different inverse transform. Still further, each such 0.25 increment of sphere diopter may also be associated with multiple inverse transforms corresponding to different values for the cylinder and axis components. In one example, each 0.50 increment of sphere diopter may be associated with a different inverse transform.

Figure 2:
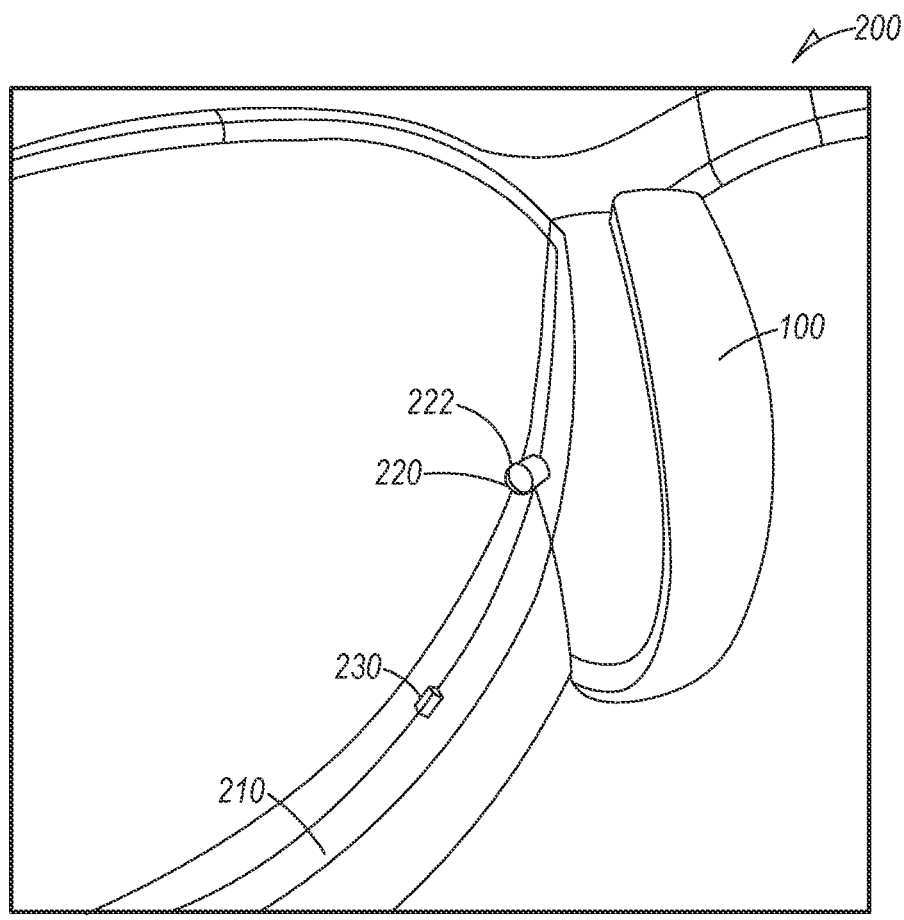
FIG. 2 is a perspective view of a portion of a headset according to an example embodiment.

FIG. 2 is a perspective view of a portion of a headset 200 having a lens 210 and a camera 220 supported by a nose pad 225. The camera 220 may be partially embedded in the nose pad 225 and is supported to have a field of view of an eye of the wearer of the headset 200 through the lens 210. An objective lens 222 of the camera 220 is also visible. In one example, the field of view of the camera 220 may be about 70 degrees. The field of view in further examples is sufficient to capture eye positions over all possible eye positions when the headset 200 is worn, as well as capture any marker supported by the lens 210. One or more light emitting diodes 230 may be supported by the headset 200 to provide IR illumination of a marker on lens 210 as shown in FIG. 1 at 135.

In a further example lenses 120 and 210 may be part of separate eyeglasses that a user wears. In this further example, the headset 200 may be configured to fit over the eyeglasses with the camera positioned to capture IR markers on the camera that may be illuminated via IR light emitting diodes.

Figure 3:
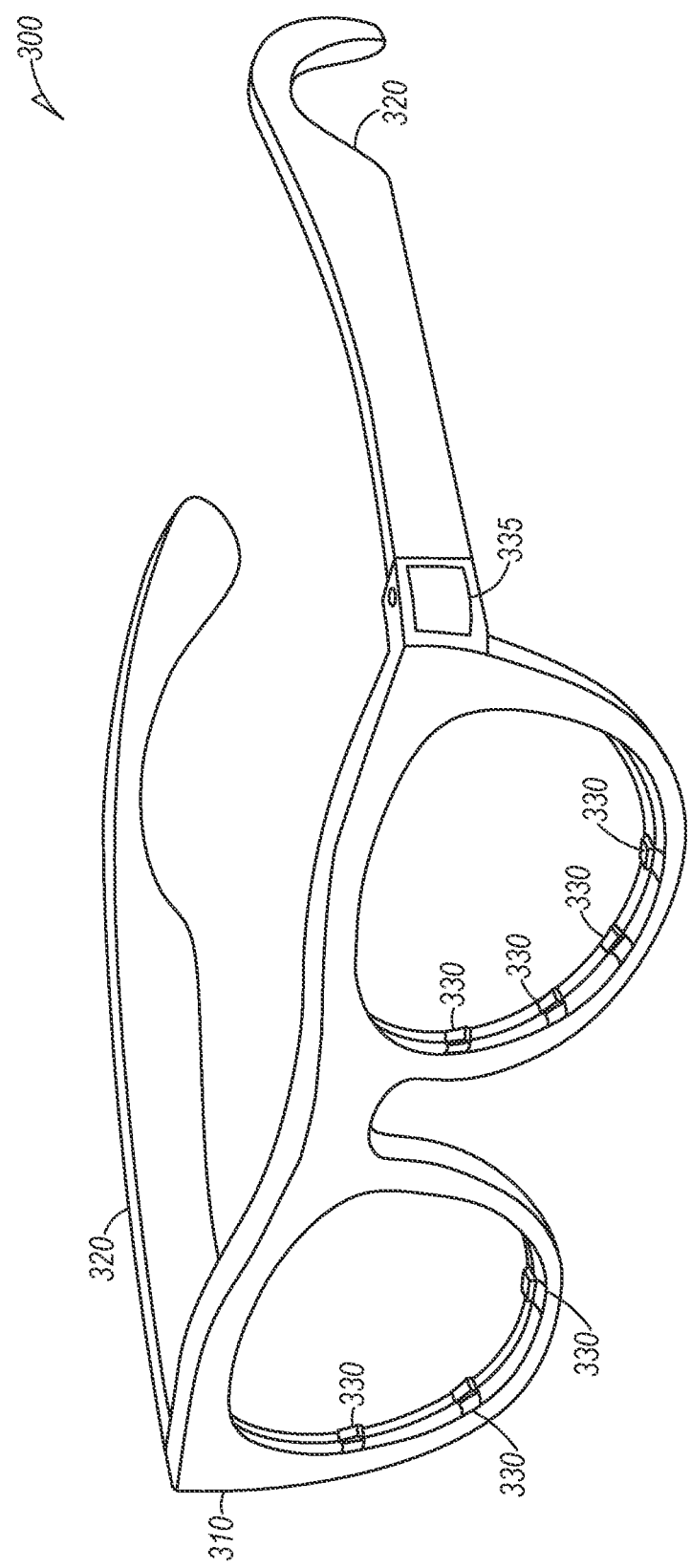
FIG. 3 is a perspective view of a headset having the shape of glasses according to an example embodiment.

FIG. 3 is a perspective view of a headset 300 having the shape of glasses. Headset 300 includes a frame 310 for holding one or more see-through displays and optional vision correcting lenses as described above. The frame 310 has openings 315 and 320 for right and left eyes of a user respectively. The openings are each configured to hold a see-through display screen. In further examples, one continuous see-through display screen may be supported by frame 310 as opposed to two separate screens.

The frame 310 supports one or more light emitting diodes indicated at 325 for illuminating markers on one or more vision correcting lenses that frame 310 is configured to support. The light emitting diodes may emit IR light for reflection by markers that are IR reflective in one example. Stems 320 are configured to help support the frame 310 on a user's head. The stems 320 extend toward ears of a user to help support the headset 300 in a proper position.

The stems 320 may support circuitry 335 for processing imaged obtained through a vision correcting lens using an inverse transform function to correct the images. Circuity 335 also performs eye tracking functions on the corrected images and further interfaces with MR, AR, and VR applications which may be locally or remotely hosted, or a combination of both remote and local hosting. In one example, the circuitry 335 may include memory pre-programmed with the proper inverse transform for the user's prescription.

Figure 4:
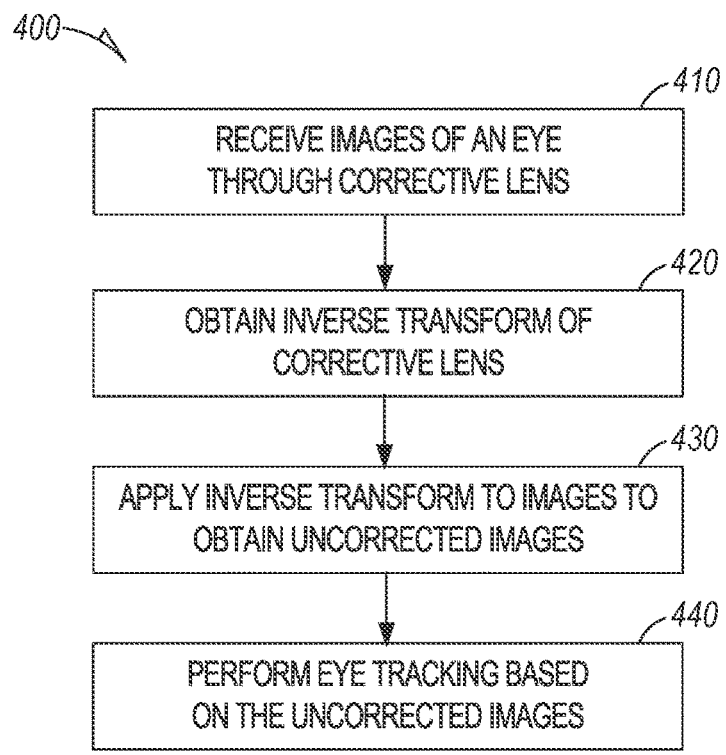
FIG. 4 is a flowchart of a computer implemented method for correcting eye tracking images according to an example embodiment.

FIG. 4 is a flowchart of a computer implemented method 400 for correcting eye tracking images. Method 400 begins at operation 410 by receiving images of an eye through a vision correcting lens via a camera in a head mounted display device. An inverse transform corresponding to the vision correcting lens is obtained at operation 420. At operation 430, the inverse transform is applied to the received images to obtain uncorrected images of the eye. Uncorrected images are images of the eye are images that would be obtained as if there was no vision-correcting lens present. Eye tracking is performed at operation 440 based on the uncorrected images of the eye.

Figure 5:
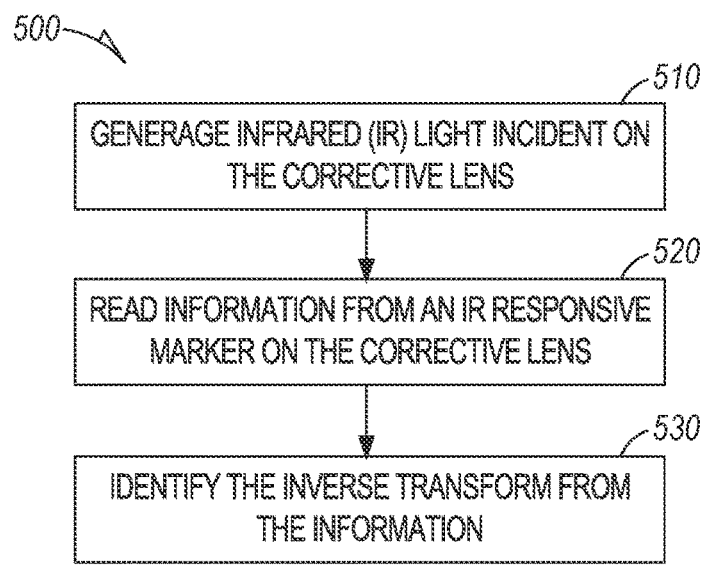
FIG. 5 is a flowchart of a computer implemented method for utilizing markers to obtain correction information for correcting eye tracking images according to an example embodiment.

FIG. 5 is a flowchart of a computer implemented method 500 for utilizing markers to obtain correction information for correcting eye tracking images. The correction information may be or identify an inverse transform function. Method 500 begins at operation 510 by generating light incident on a vision correcting lens. In one example ambient visible light may be used to provide the incident light. In a further example the light may be IR light. Information is read from a light responsive marker on the vision correcting lens captured from the images at operation 520. The marker may reflect visible or IR light in different examples. At operation 530, the inverse transform is identified from the information read from the marker.

In one example, the information comprises a vision correcting lens prescription. The inverse transform may be identified by indexing a lookup table using the prescription to identify a corresponding inverse transform. In a further example, the inverse transform may be obtained from memory associated with the head mounted display. The inverse transform may be programmed into the memory based on a prescription for a user prior to shipping the head mounted display to the user. In further examples, the user may obtain the proper inverse transform by downloading it from a database of inverse transforms corresponding to various prescriptions.

Figure 6:
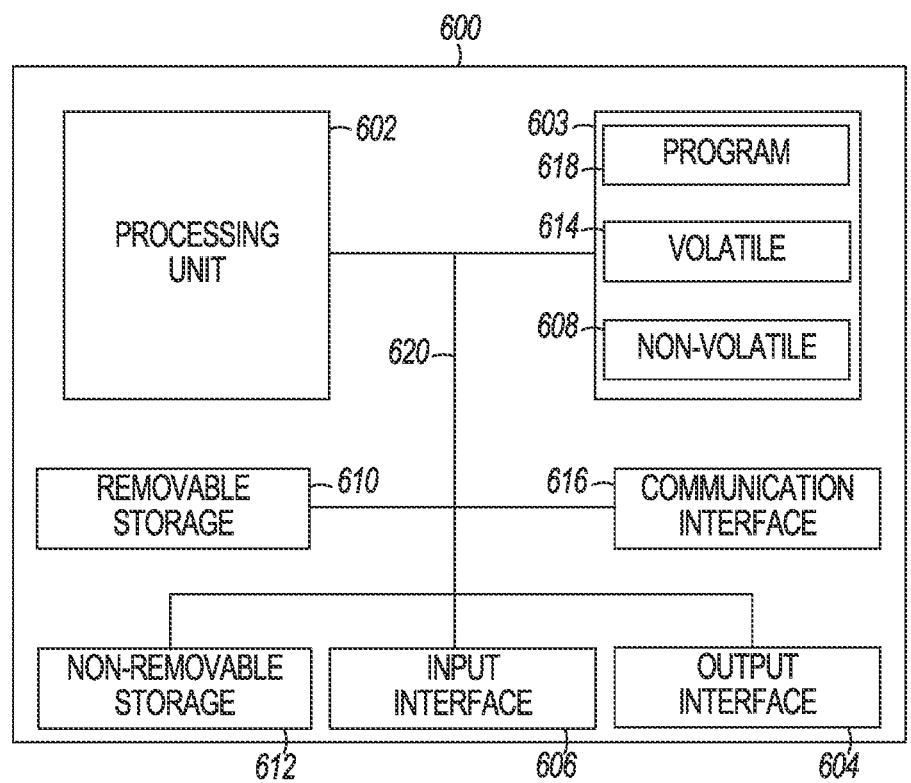
FIG. 6 is a block schematic diagram of a computer system to implement one or more example embodiments.

FIG. 6 is a block schematic diagram of a computer system 600 to implement head mounted display functions including image correction and eye tracking, and for performing methods and algorithms according to example embodiments. All components need not be used in various embodiments.

One example computing device in the form of a computer 600 may include a processing unit 602, memory 603, removable storage 610, and non-removable storage 612. Although the example computing device is illustrated and described as computer 600, the computing device may be in different forms in different embodiments. For example, the computing device may instead be a smartphone, a tablet, smartwatch, smart storage device (SSD), or other computing device including the same or similar elements as illustrated and described with regard to FIG. 6. Devices, such as smartphones, tablets, and smartwatches, are generally collectively referred to as mobile devices or user equipment.

Although the various data storage elements are illustrated as part of the computer 600, the storage may also or alternatively include cloud-based storage accessible via a network, such as the Internet or server-based storage. Note also that an SSD may include a processor on which the parser may be run, allowing transfer of parsed, filtered data through I/O channels between the SSD and main memory.

Memory 603 may include volatile memory 614 and non-volatile memory 608. Computer 600 may include—or have access to a computing environment that includes—a variety of computer-readable media, such as volatile memory 614 and non-volatile memory 608, removable storage 610 and non-removable storage 612. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 600 may include or have access to a computing environment that includes input interface 606, output interface 604, and a communication interface 616. Output interface 604 may include a display device, such as a touchscreen, that also may serve as an input device. The input interface 606 may include one or more of a touchscreen, touchpad, mouse, keyboard, camera, one or more device-specific buttons, one or more sensors integrated within or coupled via wired or wireless data connections to the computer 600, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 600 are connected with a system bus 620.

Computer-readable instructions stored on a computer-readable medium are executable by the processing unit 602 of the computer 600, such as a program 618. The program 618 in some embodiments comprises software to implement one or more methods described herein. A hard drive, CD-ROM, and RAM are some examples of articles including a non-transitory computer-readable medium such as a storage device. The terms computer-readable medium, machine readable medium, and storage device do not include carrier waves or signals to the extent carrier waves and signals are deemed too transitory. Storage can also include networked storage, such as a storage area network (SAN). Computer program 618 along with the workspace manager 622 may be used to cause processing unit 602 to perform one or more methods or algorithms described herein.

Examples

1. A computer implemented method includes receiving images of an eye through a vision correcting lens via a camera in a head mounted display device, obtaining an inverse transform corresponding to the vision correcting lens, applying the inverse transform to the received images to obtain uncorrected images of the eye, and performing eye tracking based on the uncorrected images of the eye.

2. The method of example 1 wherein obtaining an inverse transform includes reading information from a marker on the vision correcting lens from the images and identifying the inverse transform from the information.

3. The method of example 2 wherein the information includes a prescription.

4. The method of example 3 wherein identifying the inverse transform comprises indexing a lookup table using the prescription to identify a corresponding inverse transform.

5. The method of any of examples 2-3 wherein the camera is mounted between a display and the vision correcting lens.

6. The method of example 5 wherein the camera has an objective lens mounted less than 2 cm from the vision correcting lens.

7. The method of example 6 wherein the camera has a field of view of at least 70 degrees.

8. The method of any of examples 2-7 wherein the marker comprises a QR code encoding the information, and wherein the information comprises vision correcting information used to identify the inverse transform.

9. The method of example 8 wherein the QR code is a 4 mm×4 mm QR code.

10. The method of example 1 wherein the head mounted display device includes smart glasses having a nose pad, wherein the camera is mounted in the nose support and is disposed between a display screen and the vision correcting lens and wherein the IR responsive marker is supported by the vision correcting lens within a field of view of the camera.

11. The method of example 1 wherein obtaining an inverse transform includes generating infrared light (IR) incident on the vision correcting lens, reading information from an IR responsive marker on the vision correcting lens from the images, and identifying the inverse transform from the information.

12. The method of any of examples 1-9 wherein the head mounted display device includes smart glasses having a nose pad, wherein the camera is mounted in the nose support and is disposed between a display screen and the vision correcting lens.

13. The method of example 1 wherein the inverse transform is obtained from memory associated with the head mounted display.

14. A machine-readable storage device has instructions for execution by a processor of a machine to cause the processor to perform operations to perform any of the methods of examples 1-13.

15. A device includes a processor and a memory device coupled to the processor and having a program stored thereon for execution by the processor to perform operations to perform any of the methods of examples 1-13.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A computer implemented method comprising:
   receiving images of an eye through a vision correcting lens via a camera in a head mounted display device;
   obtaining an inverse transform corresponding to the vision correcting lens;
   applying the inverse transform to the received images to obtain uncorrected images of the eye; and
   performing eye tracking based on the uncorrected images of the eye.

2. The method of claim 1 wherein obtaining an inverse transform comprises:
   reading information from a marker on the vision correcting lens from the images; and
   identifying the inverse transform from the information.

3. The method of claim 2 wherein the information comprises a prescription.

4. The method of claim 3 wherein identifying the inverse transform comprises indexing a lookup table using the prescription to identify a corresponding inverse transform.

5. The method of claim 2 wherein the camera is mounted between a display and the vision correcting lens.

6. The method of claim 5 wherein the camera has an objective lens mounted less than 2 cm from the vision correcting lens.

7. The method of claim 6 wherein the camera has a field of view of at least 70 degrees.

8. The method of claim 2 wherein the marker comprises a QR code encoding the information, and wherein the information comprises vision correcting information used to identify the inverse transform.

9. The method of claim 8 wherein the QR code is a 4 mm×4 mm QR code.

10. The method of claim 2 wherein the head mounted display device comprises smart glasses having a nose pad, wherein the camera is mounted in the nose pad and is disposed between a display screen and the vision correcting lens and wherein the marker is supported by the vision correcting lens within a field of view of the camera.

11. The method of claim 1 wherein obtaining an inverse transform comprises:
   generating infrared light (IR) incident on the vision correcting lens;
   reading information from an IR responsive marker on the vision correcting lens from the images; and
   identifying the inverse transform from the information.

12. The method of claim 1 wherein the head mounted display device comprises smart glasses having a nose pad, wherein the camera is mounted in the nose pad and is disposed between a display screen and the vision correcting lens.

13. The method of claim 1 wherein the inverse transform is obtained from memory associated with the head mounted display.

14. A non-transitory machine-readable storage device having instructions for execution by a processor of a machine to cause the processor to perform operations to perform a method, the operations comprising:
   receiving images of an eye through a vision correcting lens via a camera in a head mounted display device;
   obtaining an inverse transform corresponding to the vision correcting lens;
   applying the inverse transform to the received images to obtain uncorrected images of the eye; and
   performing eye tracking based on the uncorrected images of the eye.

15. The device of claim 14 wherein the camera is mounted between a display and the vision correcting lens and wherein obtaining an inverse transform comprises:
   reading information from a marker on the vision correcting lens from the images; and
   identifying the inverse transform from the information.

16. The device of claim 15 wherein identifying the inverse transform comprises indexing a lookup table using the information to identify a corresponding inverse transform.

17. The device of claim 15 wherein the marker comprises a QR code encoding the information, and wherein the information comprises vision correcting information used to identify the inverse transform.

18. The device of claim 14 wherein obtaining an inverse transform comprises:
   generating infrared light (IR) incident on the vision correcting lens;
   reading information from an IR responsive marker on the vision correcting lens from the images; and
   identifying the inverse transform from the information.

19. A device comprising:
   a processor; and
   a memory device coupled to the processor and having a program stored thereon for execution by the processor to perform operations comprising:
      receiving images of an eye through a vision correcting lens via a camera in a head mounted display device;
      obtaining an inverse transform corresponding to the vision correcting lens;
      applying the inverse transform to the received images to obtain uncorrected images of the eye; and
      performing eye tracking based on the uncorrected images of the eye.

20. The device of claim 19 wherein obtaining an inverse transform comprises:
   generating infrared light (IR) incident on the vision correcting lens;
   reading information from an IR responsive marker on the vision correcting lens from the images; and
   identifying the inverse transform from the information.

* * * * *